(12) United States Patent
Dent et al.

(10) Patent No.: US 7,888,341 B2
(45) Date of Patent: Feb. 15, 2011

(54) COMBINATION OF GLIVEC (STI571) WITH A CYCLIN-DEPENDENT KINASE INHIBITOR, ESPECIALLY FLAVOPIRIDOL, IN THE TREATMENT OF CANCER

(75) Inventors: Paul Dent, GlenAllen, VA (US); Steven Grant, Richmond, VA (US); Geoffrey Krystal, Richmond, VA (US); Chunrong Yu, Richmond, VA (US)

(73) Assignees: The United States of America as represented by the Department of Veterans Affairs, Washington, DC (US); Virginia Commonwealth University, Richmond, VA (US)

( * ) Notice: Subject to any disclaimer, the term of this patent is extended or adjusted under 35 U.S.C. 154(b) by 745 days.

(21) Appl. No.: 10/510,531

(22) PCT Filed: Apr. 4, 2003

(86) PCT No.: PCT/IB03/01418

§ 371 (c)(1),
(2), (4) Date: Mar. 30, 2005

(87) PCT Pub. No.: WO03/084543

PCT Pub. Date: Oct. 16, 2003

(65) Prior Publication Data

US 2005/0176725 A1    Aug. 11, 2005

Related U.S. Application Data

(60) Provisional application No. 60/371,330, filed on Apr. 10, 2002.

(51) Int. Cl.
*A01N 43/58* (2006.01)
*A61K 31/50* (2006.01)

(52) U.S. Cl. ...................................... 514/183; 514/247

(58) Field of Classification Search .................. 514/183, 514/247

See application file for complete search history.

(56) References Cited

U.S. PATENT DOCUMENTS

2002/0147197 A1    10/2002    Newman et al. ......... 514/235.8

FOREIGN PATENT DOCUMENTS

WO    WO 01/26467    4/2001

OTHER PUBLICATIONS

Yu et. al., The cyclin dependent kinase inhibitor flavopiridol interacts synergistically with the BCR/ABL kinase inhibitor STI571 to induce mitochondrial damage and apoptosis in BCR/ABL+ human leukemia cells; Blood, (2001), 98:146a.*
Gura et. al. (Science, 1997, 278:1041-1042).*
Johnson et. al. (British Journal of Cancer, 2001, 84:1424-1431).*
Shah et. al. (Expert Opinion on Investigational Drugs (2005) 14:89-91).*
O'Hare (Expert Opinion on Investigational Drugs (2008) 17:865-878).*
Fabbro et al., "Protein Kinases as Targets for Anticancer Agents: from Inhibitors to Useful Drugs", *Pharmacol Thera*, vol. 93, Nos. 2-3, pp. 79-98 (2002).
Workman, "The Impact of Genomic and Proteomic Technologies on the Development of New Cancer Drugs", *Ann Oncol*, vol. 13, No. 12, Suppl. 4, pp. 115-124 (2002).
Yanovich, Hall and Gewirtz, "Characterization of a K562 Multidrug-resistant Cell Line", *Cancer Res*, vol. 49, No. 16, pp. 4499-4501 (1989).
Yu et al., "Pharmacologic Mitogen-activated Protein/Extracellular Signal-regulated Kinase Kinase/Mitogen-activated Protein Kinase Inhibitors Interact Synergistically with STI571 to Induce Apoptosis in BCR/ABL-expressing Human Leukemia Cells", *Cancer Res*, vol. 62, No. 1, pp. 188-199 (2002).
Yu, Krystal, Dent and Grant, "Flavopiridol Potentiates STI571-induced Mitochondrial Damage and Apoptosis in BCR-ABL-positive Human Leukemia Cells", *Clin Cancer Res*, vol. 8, No. 9, pp. 2976-2984 (2002).

* cited by examiner

*Primary Examiner*—Brandon J Fetterolf
*Assistant Examiner*—Marcos Sznaidman
(74) *Attorney, Agent, or Firm*—George R. Dohmann

(57) ABSTRACT

The present invention pertains to a combination for simultaneous, separate or sequential use which comprises (a) a cyclin-dependent kinase inhibitor and (b) 4-(4-methylpiperazin-1-ylmethyl)-N-[4-methyl-3-(4-pyridin-3-yl)pyrimidin-2-ylamino)phenyl]-benzamide and to its use for the treatment of cancer, especially of Bcr/Abl$^+$ leukemia resistant to compound of formula I.

6 Claims, No Drawings

COMBINATION OF GLIVEC (STI571) WITH A CYCLIN-DEPENDENT KINASE INHIBITOR, ESPECIALLY FLAVOPIRIDOL, IN THE TREATMENT OF CANCER

This application claims benefit of U.S. Provisional Application 60/371,330, filed Apr. 10, 2002.

The invention relates to a pharmaceutical combination which comprises (a) a cyclin-dependent kinase (CDK) inhibitor and (b) 4-(4-methylpiperazin-1-ylmethyl)-N-[4-methyl-3-(4-pyridin-3-yl)pyrimidin-2-ylamino)phenyl]-benzamide (hereinafter: "COMPOUND I") and optionally at least one pharmaceutically acceptable carrier for simultaneous, separate or sequential use, in particular for the treatment of a proliferative disease, especially a tumor disease; a pharmaceutical composition comprising such a combination; the use of such a combination for the preparation of a medicament for the treatment of a proliferative disease; a commercial package or product comprising such a combination as a combined preparation for simultaneous, separate or sequential use; and to a method of treatment of a warm-blooded animal, especially a human.

The Bcr/Abl oncogene encodes a fusion protein that is found in the cells of 95% of patients with chronic myelogenous leukemia (CML). Constitutive activation of the Bcr/Abl tyrosine kinase confers a survival advantage to hematopoietic cells, contributing to leukemic transformation. More specifically, expression of the Bcr/Abl kinase renders cells relatively insensitive to apoptosis induced by diverse stimuli, including growth factor deprivation and cytotoxic drugs. Recently, considerable attention has focused on COMPOUND I, a tyrosine kinase inhibitor that inhibits the Bcr/Abl, c-Kit, and to a lesser extent, other kinases. SALT I (the monomesylate salt of COMPOUND I) has been shown to inhibit the growth of and induce apoptosis in Bcr/Abl-positive leukemia cells in vitro. Significantly, oral administration of SALT I to patients with CML results in clinical responses in the large majority of patients. However, the emergence of SALT I resistance in CML patients initially responsive to this agent has prompted the search for alternative approaches to the treatment of this disease.

The present invention reports that a combination therapy of an Bcr/Abl+ leukemia resistant to SALT I characterized by the over expression of Bcr/Abl, comprising a therapeutically effective amount of a CDK inhibitor, particularly flavopiridol (FP) and a therapeutically effective amount of SALT I, can produce a therapeutic effect which is greater than that obtainable by a single administration of a therapeutically effective amount of either a sole CDK inhibitor or the sole SALT I.

The present invention pertains to a combination for simultaneous, separate or sequential use, such as a combined preparation or a pharmaceutical fixed combination, which comprises (a) cyclin-dependent kinase inhibitor and (b) COMPOUND I in which the active ingredients (a) and (b) are present in each case in free form or in the form of a pharmaceutically acceptable salt, and optionally at least one pharmaceutically acceptable carrier.

The present invention pertains to a combination for simultaneous, separate or sequential use, such as a combined preparation or a pharmaceutical fixed combination, which comprises synergistically effective amounts of (a) cyclin-dependent kinase inhibitor and (b) COMPOUND I in which the active ingredients (a) and (b) are present in each case in free form or in the form of a pharmaceutically acceptable salt, and optionally at least one pharmaceutically acceptable carrier.

All the WO (number) references are meant to refer to the WIPO publications of the PCT patent applications of the corresponding references.

The monomethanesulfonic acid addition salt of COMPOUND I (hereinafter "SALT I") and a preferred crystal form thereof are described in WO 99/03854 published on Jan. 28, 1999.

Most of the CDK inhibitors act on CDK 1, 2, 4, 6 or 7 or are able of inhibiting several of those kinases. Examples of CDK inhibitors according to the invention are nucleic acid encoding for inhibitors of CDKs, peptides and peptidomimetic inhibitors, peptide aptamers, small molecules such as flavonoids, purine derivatives, pyrimidine derivatives, butyrolactone1, indigoid bisindole derivatives, benzenesulfonamides, thiazole derivatives, paullones derivatives, staurosporine derivatives, pyrazolopyridine compounds, indol derivatives, amino-pyrazole compounds.

Nucleic acid encoding for CDK inhibitors are disclosed in U.S. Pat. No. 5,621,082 and WO 99/06540. Peptides and peptidomimetic inhibitors are described in EP 0 666 270 A2, Bandara et al., Nature Biotechnology 1997, 15, 896-901 and Chen et al., Proc. Natl. Acad. Sci. USA, 1999, 96, 4325-29. Peptide aptamers are disclosed in Cohen et al., Proc. Natl. Acad. Sci. USA 1998, 95, 14272-77. Small molecules are reviewed in Exp. Opin. Invest. Drugs 1998, 7, 865-87 and Curr. Opin. in Drug Discov. & Devel. 1999, 2, 274-85.

Flavonoids according to the invention are catechins, genistein and antibody-genistein conjugates, e.g. B43-genistein and (epidermal growth factor) EGF-genistein, quercetin, flavopiridol and flavopiridol derivatives.

Flavopiridol (L86-8275, HMR 1275) is a semi-synthetic flavone, derived from the flavonoid rohitukine and is described in U.S. Pat. No. 4,900,727, EP241003 and Int. J. Oncology 1996, 9, 1143-1168. Flavopiridol is 4H-1-benzopyran-4-one,2-(2-chlorophenyl)-5,7-dihydroxy-8-(3-hydroxy-1-methyl-4-piperidinyl)-,hydrochloride, (−)-cis-. Flavopiridol acts as potent inhibitor of multiple cyclin-dependent kinases (CDKs), including CDK1, 2, 4/6, and 7.

Flavopiridol derivatives such as thio- and oxoflavopiridols are disclosed in J. Med. Chem. 2000, 43, 4126-4134, flavopiridol analogs are described in U.S. Pat. No. 5,733,920, WO 97/42949 and WO 98/17662.

Purine derivatives according to the invention are described in Bioorg. Med. Chem. Lett. 1997, 7, 2697-2702; Proc. Amer. Assoc. Cancer Res. 1998, 39, 1207; Bioorg. Med. Chem. Lett. 1998, 8, 793-98; Science 1998, 281, 533-38; Chemistry & Biology 1999, 6, 361-75. 2, 6, 9-trisubstituted purines are disclosed in U.S. Pat. No. 6,316,456 B1, J. Med. chem. 1997, 40: 408-12 especially olomoucine, bohemine is described in Drug. Metab. Dispos. 2001, 3, 326-34, CVT 313 is described in J. Biol. Chem. 1997, 272:29207-211, CVT 2584 and CVT 2454 are disclosed in MEDI, 2000, 136:26, purvalanol B, R-roscovitine (CYC 202, 2-(R)-1-ethyl-2-hydroxyethylamino)-6-benzylamino-9-isopropylpurine), 2,6-disubstituted purines, e.g. NU 2058, WO 99/02162, 6,9-disubstituted purines are described in WO 99/43675 and WO 99/43676.

The term "pyrimidine-based derivative" includes but is not restricted to compounds as described in J. Med. Chem. 2000, 43, 2797-2804, e.g. NU 6027 and NU 6034 and in 91st Annual Meeting of the American Association for Cancer Research. 2000, 41:314 (PD 0183812) as well as in WO 98/33798, Proc. Amer. Assoc. Cancer Res. 1998, 39, Abst. 3796 and Proc. Amer. Assoc. Cancer Res. 1998, 39, Abst. 3794.

The term "paullone derivatives" means compounds as described in Int. J. Chem. 1999, 42, 2909-2919 and Cancer Research 1999, 59:2566-2569, e.g. alsterpaullone (NSC 705701, 9-nitropaullone) and kenpaullone (NSC 664704, 9-bromopaullone).

The term "benzenesulfonamides" includes but is not restricted to compounds as described in Owa et al., J. Med. Chem., 1999, 42, 3789-99, especially, E 7070 (ER-35744).

Thiazole derivatives are amino- and isothiazoles as described in U.S. Pat. No. 6,040,321, U.S. Pat. No. 6,262,096, WO 99/24416, WO 99/21845 and WO 99/62890, especially AG 12286 and AG 12275 (MEDI 1999, 214).

A staurosporine derivative is in particular staurosporine, LY 333531, MLR52, UCN-01 (7-hydroxy-staurosporine), UCN-02, midostaurin (EP0296110), NA 382, 2-methyl K252a, K-252a (J. Cell. biol 1991, 115:1275), KT-5720, Ro-31-8425, Ro-31-7549 and Ro-31-8220.

Indigoid bisindole derivatives are described in WO 99/62503 and WO 00/61555.

Pyrazolopyridine inhibitors are disclosed in MEDI 2000, 38 especially BMS 265246.

Indol derivatives according to the invention are SU9516 ((Z)-3-(1H-Imidazol-5-ylmethylene)-5-methoxy-2,3-dihydro-1H-indol-2-one), oxindole inhibitors are described in 90th and 91st Annual Meeting Amer. Assoc. Cancer Res. 1999, 724; 2000, 41:31, in Luzzio et al., 1999 Abst. 4102, in Inpharma. 2000, 1237: 7-8 in Expert Opinion on Investigational Drugs 8:903-9 and in WO 99/15500, especially GW 2059, GW 8510, GW 5181 and GW 9499.

Amino-pyrazole compounds are disclosed in U.S. Ser. No. 09/835,566.

NSC 373853, NSC 373854, NSC 625987 and NSC 645787 are reported in the Annual Meeting of the Amer. Soc. Clinic. Oncology, 1997, 212.

Surprisingly, FP interacts with COMPOUND I, e.g. SALT I in a highly synergistic manner to trigger mitochondrial injury and apoptosis in such cells, including those resistant to COMPOUND I and displaying Bcr/Abl amplification. Unexpectedly, it has been found that the anti-proliferative effect on tumors of a combination comprising FP and COMPOUND I is greater than the maximum effect that can be achieved with either type of ingredient alone.

The present results indicate that the CDK inhibitor flavopiridol markedly increases SALT I-mediated mitochondrial damage and apoptosis in Bcr/Abl+ leukemic cells, including SALT I-resistant K562 cells, especially K562R cells that express increased levels of the Bcr/Abl protein.

The invention pertains to a combination wherein the cyclin-dependent kinase inhibitor is selected from the group consisting of FP, CYC 202 and E 7070.

The term "a combined preparation", as used herein defines especially a "kit of parts" in the sense that the combination partners (a) and (b) as defined above can be dosed independently of each other or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

The term "treatment" comprises the administration of the combination partners to a warm-blooded animal in need of such treatment with the aim to cure the tumor or to have an effect on tumor regression or on the delay of progression of a disease.

The term "delay of progression" as used herein means that the tumor growth or generally, the disease progression is at least slowed down or hampered by the treatment and that patients exhibit higher survival rates than patients not being treated or being treated with the monotherapy.

The term "proliferative disease" includes but is not restricted to tumors, psoriasis, restenosis, sclerodermitis and fibrosis.

The term "tumor disease" means any neoplastic proliferative disorder e.g. solid tumor diseases or liquid tumor diseases.

The term "liquid tumor disease" as used herein includes, but is not limited to, chronic myelogenous leukemia and acute lymphocyte leukemia (ALL), especially the Philadelphia chromosome positive acute lymphocyte leukemia (Ph+ALL) as well as SALT I-resistant leukemia.

The term "SALT I-resistant leukemia" as used herein defines especially a leukemia in which SALT I shows a reduction of its therapeutic effectiveness, it includes but is not restricted to leukemia exhibiting resistance to SALT I treatment by Bcr/Abl gene amplification, increased expression of Bcr/Abl protein and Abl kinase domain mutation.

The term "a solid tumor disease" especially means ovarian cancer, breast cancer, cancer of the colon and generally the gastrointestinal tract, cervix cancer, lung cancer, e.g. small-cell lung cancer and non-small-cell lung cancer, head and neck cancer, bladder cancer, cancer of the prostate or Kaposi's sarcoma.

The combination partner (b) COMPOUND I is 4-(4-methylpiperazin-1-ylmethyl)-N-[4-methyl-3-(4-pyridin-3yl)pyrimidin-2-ylamino)phenyl]-benzamide having the formula I

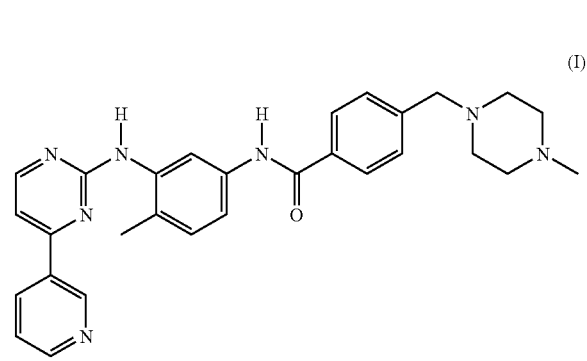

(I)

It can be prepared and administered as described in WO 99/03854.

The structure of the active agents cited may be taken from the actual edition of the standard compendium "The Merck Index" or from databases, e.g. Patents International (e.g. IMS World Publications). The corresponding content thereof is hereby incorporated by reference. Any person skilled in the art is fully enable, based on these references, to manufacture and test the pharmaceutical indications and properties in standard test models, both in vitro and in vivo.

It will be understood that references to the combination partners (a) and (b) are meant to also include their respective pharmaceutically acceptable salts. If the combination partner has at least one basic group, it can form acid addition salts. The combination partner having an acid group (for example COOH) can also form salts with bases. The combination partner (a) or (b) or a pharmaceutically acceptable salt thereof may also be used in form of a hydrate or include other solvents used for crystallization. The 4-(4-methylpiperazin-1-ylmethyl)-N-[4-methyl-3-(4-pyridin-3-yl)pyrimidin-2-ylamino) phenyl]-benzamide, i.e. combination partner (a), is preferably used in the present invention in the form of its monomesylate salt.

A combination which comprises (a) a CDK inhibitor and (b) COMPOUND I in which the active ingredients are present in each case in free form or in the form of a pharmaceutically acceptable salt and optionally at least one pharmaceutically acceptable carrier, will be referred to hereinafter as a COMBINATION OF THE INVENTION.

The COMBINATIONS OF THE INVENTION inhibit the growth of solid tumors, but also liquid tumors. Furthermore, the COMBINATIONS OF THE INVENTION exhibit beneficial effects in the treatment of diseases associated with deregulated angiogenesis. In one preferred embodiment of the invention, the proliferative disease to be treated with a COMBINATION OF THE INVENTION is leukemia, especially Bcr/Abl+ leukemia and preferably SALT I-resistant leukemia.

All the more surprising is the experimental finding that in vivo the administration of a COMBINATION OF THE INVENTION compared to a monotherapy applying only one of the pharmaceutically active ingredients used in the COMBINATION OF THE INVENTION results not only in a more beneficial, especially synergistic, e.g. anti-proliferative effect, e.g. with regard to the delay of progression of a proliferative disease or with regard to a change in tumor volume, but also in further surprising beneficial effects, e.g. less side-effects and a decreased mortality and morbidity. The COMBINATIONS OF THE INVENTION are suitable in particular in the treatment of proliferative diseases refractory to chemotherapeutics known as anti-cancer agents as well as proliferative diseases refractory to SALT-I treatment The COMBINATIONS OF THE INVENTION are also suitable to prevent the metastatic spread of tumors and the growth or development of micro metastases.

A further benefit is that lower doses of the active ingredients of the COMBINATION OF THE INVENTION can be used, for example, that the dosages need not only often be smaller but are also applied less frequently, or can be used in order to diminish the incidence of side-effects like, e.g., diarrhea or nausea observed with one of the combination partners alone. This is in accordance with the desires and requirements of the patients to be treated.

It can be shown by established test models that a COMBINATION OF THE INVENTION results in the beneficial effects described herein before. The person skilled in the pertinent art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are in particular randomized, double-blind, placebo-controlled, parallel studies in cancer patients with late stage disease. Such studies are, in particular, suitable to compare the effects of a monotherapy using the active ingredients and a therapy using a COMBINATION OF THE INVENTION, and to prove in particular the synergism of the active ingredients of the COMBINATIONS OF THE INVENTION. The primary endpoints in such studies can be the effect on pain scores, analgesic use, performance status, Quality of Life scores or time to progression of the disease. The evaluation of tumors by in regular time periods, e.g. every 4, 6 or 8 weeks, is a suitable approach to determine the effect of the COMBINATION OF THE INVENTION. In a suitable study design, patients are, for example, receiving per treatment cycle of 2 weeks, SALT I daily at a dose ranging from 50 to 800 mg of the active substance and FP at a dose ranging from 5 to 75 mg/m$^2$/day for 3 days. The minimum duration of such a study should be about, e.g. 4 weeks.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application. In one embodiment of the invention, one or more of the active ingredients are administered intravenously.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners of the COMBINATION OF THE INVENTION may be administered simultaneously or sequentially and in any order, and the components may be administered separately or as a fixed combination. For example, the method of delay of progression or treatment of a proliferative disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

Flavopiridol can be administered at a dose range of 10 to 100 mg/m$^2$/day, preferably at a dose range of 10 to 50 mg/m$^2$/day, e.g. described in Clin. Cancer Res. 2001, 7, 1590-9, e.g. a 72 hour continuous infusion every 14 days at a dose of 50 mg/m$^2$/day at a concentration of 0.1 to 0.2 mg/ml. Alternatively, FP can be administered at a preferred dose of 78 mg/m$^2$/day for 3 days every 2 weeks with anti-diarrheal prophylaxis.

119.5 mg of SALT I correspond to 100 mg of COMPOUND I (free base) as active substance. Depending on species, age, individual condition, mode of administration, and the clinical picture in question, effective doses of SALT I, for example daily doses corresponding to about 50 to 1000 mg, e.g. 50 to 800 mg of the active substance, preferably 50 to 600 mg, e.g. 50 to 400 mg, are administered to warm-blooded animals of about 70 kg bodyweight. For adult patients with leukemia, a starting dose of 400 mg daily can be recommended. For patients with an inadequate response after an assessment of response to therapy with 400 mg daily, dose escalation can be safely considered and patients may be treated as long as they benefit from treatment and in the absence of limiting toxicities.

For example, FP and SALT I are synergistically effective in a molar ratio (FP:SALT I) range of 1:1 to 1:20, preferably 1:10, e.g. 1:1.33.

The invention relates also to a method for administering to a human subject suffering from a tumor disease, especially leukemia, COMPOUND I or a pharmaceutically acceptable salt thereof, which comprises administering daily a pharmaceutically effective amount of COMPOUND I or a pharmaceutically acceptable salt thereof to the human subject for a period exceeding 3 months. The invention relates especially to such method wherein a daily dose of 50 to 800 mg of the active substance, especially 50 to 600 mg, e.g. 50 to 400 mg, is administered.

When the combination partners employed in the COMBINATION OF THE INVENTION are applied in the form as marketed as single drugs, their dosage and mode of administration can take place in accordance with the information provided on the packet leaflet of the respective marketed drug in order to result in the beneficial effect described herein, if not mentioned herein otherwise.

The COMBINATION OF THE INVENTION can be a combined preparation or a pharmaceutical composition.

Moreover, the present invention relates to a method of treating a warm-blooded animal having a proliferative disease comprising administering to the animal a COMBINATION OF THE INVENTION in a quantity which is jointly therapeutically effective against a proliferative disease and in which the combination partners can also be present in the form of their pharmaceutically acceptable salts. In one embodiment of the invention, in such method the COMBINATION OF THE INVENTION is co-administered with an anti-diarrheal agent. Furthermore, the treatment can comprise surgery, radiotherapy, cryotherapy and immunotherapy.

The invention also relates to a method of inhibiting the formation of metastases in a warm-blooded animal having a tumor disease which comprises administering to the patient a pharmaceutically effective amount of the COMBINATION OF THE INVENTION in a quantity which is jointly therapeutically effective against said tumor disease and in which the compounds can also be present in the form of their pharmaceutically acceptable salts.

Furthermore, the present invention pertains to the use of a COMBINATION OF THE INVENTION for the treatment of a proliferative disease and for the preparation of a medicament for the treatment of a proliferative disease.

Additionally, the present invention pertains to the use of FP in combination with SALT I for the preparation of a medicament for the treatment of a proliferative disease. Moreover, the present invention provides a commercial package comprising as active ingredients COMBINATION OF THE INVENTION, together with instructions for simultaneous, separate or sequential use thereof in the treatment of a proliferative disease.

EXAMPLE 1

Cells: K562 human leukemia cells are purchased from ATCC, Rockville, Md. and are cultured in RPMI 1640 medium supplemented with sodium pyruvate, MEM essential vitamins, L-glutamate, penicillin, streptomycin, and 10% heat-inactivated fetal calf serum (Hyclone, Logan, Utah). Drug-resistant K562 cells (K562R) are derived from the parental line by sub-culturing in progressively higher concentrations of doxorubicin as previously described in Yanovich et al. The doxorubicin-resistant variant of the K562 human leukemia cell line (K562R) demonstrates cross-resistance to other anthracycline antibiotics and Vinca alkaloids. The K562R cells have a phenotype similar to that of other multidrug resistant cell lines (Yanovich et al., 1989, Cancer Res. 49, 4499-4503). They are cultured in drug-free medium prior to all experimental procedures.

Preparation of S-100 fractions: Cells are harvested after drug treatment and the cytosolic S-100 fraction isolate by ultracentrifugation as described in Yu et al., Mol. Pharmacol. 2001, 60, 143-53.

Assessment of apoptosis: Following drug exposures, cytocentrifuge preparations are stained with Wright-Giemsa and viewed by light microscopy to evaluate the extent of apoptosis as described in Wang Z. et al., 1999 Cancer Res. 59, 1259-67.

Determination of mitochrondial membrane potential ($\Delta\Psi_m$): Mitochondrial membrane potential is monitored by measuring uptake of 3,3-dihexyloxacarbocyanine iodide (DiOC$_6$) using a FACScan flow cytometer and CellQuest software (Becton Dickinson, Immunocytometry Systems, San Jose, Calif.) as previously described in Wang Z. et al., 1999 Cancer Res. 59, 1259-67.

1. Co-exposure of K562 Cells to SALT I and FP Results in a Marked Potentiation of Apoptosis (A) K562 cells were exposed for 48 h to 150 nM FP and the designated concentration of SALT I, after which the percentage of apoptotic cells was determined by morphologic assessment of Wright Giemsa-stained slides as described above. Values represent the means for three separate experiments performed in triplicate±SD (standard deviation).

| SALT I | without FP | | +FP (150 nM) | | FP | without SALT I | | +SALT I (200 nM) | |
|---|---|---|---|---|---|---|---|---|---|
| (nM) | mean | SD | mean | SD | (nM) | mean | SD | mean | SD |
| 0 | 0.7 | 0.1 | 0.9 | 0.1 | 0 | 0.7 | 0.1 | 5.7 | 0.8 |
| 50 | 1.9 | 0.0 | 2.2 | 0.2 | 50 | 1.9 | 0.1 | 12.1 | 1.7 |
| 100 | 1.8 | 0.3 | 4.9 | 0.8 | 100 | 2.4 | 0.4 | 35.8 | 3.1 |
| 150 | 3.0 | 0.1 | 22.5 | 3.1 | 150 | 3.2 | 0.7 | 56.3 | 4.5 |
| 200 | 4.6 | 0.6 | 58.1 | 4.7 | 200 | 6.1 | 1.0 | 63.7 | 5.0 |
| 250 | 8.9 | 2.0 | 62.7 | 3.6 | 300 | 18.5 | 2.2 | 77.0 | 3.2 |
| 300 | 20.3 | 3.2 | 74.0 | 3.1 | | | | | |
| 400 | 30.8 | 2.7 | 82.9 | 4.4 | | | | | |
| 500 | 53.8 | 3.5 | 85.5 | 5.7 | | | | | |

Exposure of K562 cells for 48 hr to SALT I concentrations <300 nM weakly induces apoptosis, whereas concentrations of 300-500 nM induced lethality in 20-50% of cells. However, co-administration of 150 nM FP, which is essentially non-toxic by itself (i.e., inducing <5% cell death), dramatically increases apoptosis in cells exposed to SALT I concentrations of 150 nM. Co-administration of FP at concentrations of 100 nM markedly potentiates the lethal effects of 200 nM SALT I, and these effects are particularly pronounced in the case of 300 nM FP.

(B) K562 cells were exposed to 150 nM FP+200 nM SALT I for 24 or 48 h, after which the percentage of apoptotic cells is determined as previously described. Values represent the means for three separate experiments performed in triplicate±S.D (standard deviation).

| | | control | FP (150 nM) | SALT I (200 nM) | FP + SALT I |
|---|---|---|---|---|---|
| 24 h | mean | 0.67 | 1.40 | 2.57 | 9.73 |
| | SD | 0.12 | 0.36 | 0.48 | 2.89 |
| 48 h | mean | 0.73 | 3.33 | 5.97 | 55.57 |
| | SD | 0.09 | 0.50 | 1.20 | 4.01 |

The lethal effects of 200 nM SALT I+150 nM FP, reflected by the appearance of apoptotic cells are modest after 24 h, but very extensive after 48 h, indicating a delayed mode of action for this drug combination.

2. Synergistic Induction of Apoptosis by SALT I/FP.

K562 cells are exposed to varying concentrations of FP and SALT I at a fixed ratio (1:1.33) for 48 h, after which the percentage of apoptotic cells or cells displaying a decline in $\Delta\psi_m$ is monitored as described above. The Combination Index (CI) is determined in relation to the fraction of cells affected using Median Dose Effect analysis. Results are representative of three separate experiments.

| | fraction affected | | | | |
|---|---|---|---|---|---|
| | 0.075 | 0.120 | 0.250 | 0.560 | 0.712 |
| CI - apoptosis | 0.851 | 0.790 | 0.595 | 0.345 | 0.290 |
| CI - $\Delta\psi_m$ | 0.429 | 0.311 | 0.289 | 0.256 | 0.225 |

Median Dose effect analysis is employed to characterize interactions between SALT I and FP with respect to Both Induction of Apoptosis and loss of $\Delta\psi_m$ at 48 h. Combination Index (CI) values less than 1.0 are consistently obtained, particularly in the case of loss of $\Delta\psi_m$, denoting a highly synergistic interaction between SALT I and flavopiridol.

3. Co-Exposure of Drug-Resistant K562 (K562R) Cells that Express High Levels of the Bcr/Abl Protein to SALT I and FP Results in a Pronounced Increase in Apoptosis.

K562R cells are exposed to 1.5 µM SALT I±200 nM FP for 48 h, after which the percentage of apoptotic cells is determined as described above. Values represent the means for three separate experiments performed in triplicate±S.D.

| | control | FP (200 nM) | SALT I (1.5 µM) | FP + SALT I |
|---|---|---|---|---|
| mean | 0.73 | 1.77 | 12.57 | 48.57 |
| SD | 0.12 | 0.35 | 1.62 | 3.10 |

The multi-drug resistant K562 cell line (K562R) is employed, which exhibits approximately a 300% increase in Bcr/Abl protein expression relative to the parental line. K562R cells display a marked decrease in SALT I susceptibility, with an I.C.$_{50}$ 10-fold higher than that of parental cells, e.g., ~3.0 µM versus 0.4 µM in parental K562S cells. In K562R cells, a 48-hr exposure to 150 nM FP is non-toxic, whereas 1.5 µM SALT I induced apoptosis in only ~10% of cells. In contrast, exposure of parental K562S cells to 1.5 µM SALT I for 48 hr resulted in >95% apoptosis. Significantly, combined treatment of K562R cells with SALT I and FP increases the extent of apoptosis approximately 5-fold compared to SALT I alone (i.e., to ~50%). These findings indicate that co-administration of a sub-toxic concentration of FP substantially potentiates SALT I-related lethality in resistant cells that exhibit increased levels of the Bcr/Abl protein.

EXAMPLE 2

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, β-crystal form Capsules containing 119.5 mg of the compound named in the title (=SALT I) corresponding to 100 mg of COMPOUND I (free base) as active substance are prepared in the following composition:

| Composition | |
|---|---|
| SALT I | 119.5 mg |
| Cellulose MK GR | 92 mg |
| Crospovidone XL | 15 mg |

-continued

| Composition | |
|---|---|
| Aerosil 200 | 2 mg |
| Magnesium stearate | 1.5 mg |
| | 230 mg |

The capsules are prepared by mixing the components and filling the mixture into hard gelatin capsules, size 1.

EXAMPLE 3

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate. β-crystal form Capsules containing 119.5 mg of the compound named in the title (=SALT I) corresponding to 100 mg of COMPOUND I (free base) as active substance are prepared in the following composition:

| Composition | |
|---|---|
| SALT I | 119.5 mg |
| Avicel | 200 mg |
| PVPPXL | 15 mg |
| Aerosil | 2 mg |
| Magnesium stearate | 1.5 mg |
| | 338 mg |

The capsules are prepared by mixing the components and filling the mixture into hard gelatin capsules, size 1.

What is claimed is:

1. A method of treating Bcr/Abl-positive leukemia resistant to a compound of formula I

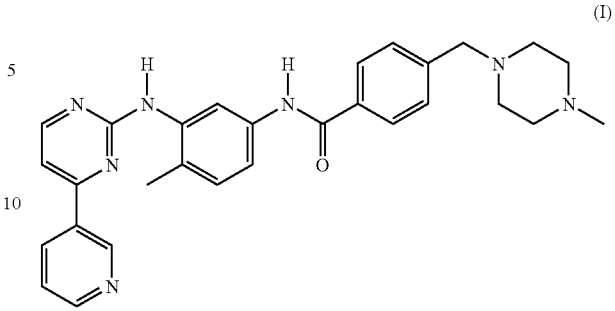

comprising 1) identifying a patient that has Bcr/Abl-positive leukemia resistant to compound of formula I, and 2) administering to a patient in need thereof a combination of (a) a cyclin-dependent kinase inhibitor and (b) 4-(4-methylpiperazin-1-ylmethyl)-N-[4-methyl-3-(4-pyridin-3-yl)pyrimidin-2-ylamino)phenyl]-benzamide in which the active ingredients (a) and (b) are present in each case in free form or in the form of a pharmaceutically acceptable salt, and optionally at least one pharmaceutically acceptable carrier, for simultaneous, separate or sequential use.

2. The method according to claim 1 wherein the Bcr/Abl-positive leukemia resistant to compound of formula I overexpresses Bcr/Abl.

3. The method according to claim 1 wherein the cyclin-dependent kinase inhibitor is flavopiridol or E 7070 or CYC 202.

4. The method according to claim 1 wherein the cyclin-dependent kinase inhibitor is flavopiridol.

5. The method according to claim 4 wherein flavopiridol and 4-(4-methylpiperazin-1-ylmethyl)-N-[4-methyl-3-(4-pyridin-3-yl)pyrimidin-2-ylamino)phenyl]-benzamide are present in a molar ratio (FP/COMPOUND I) range of 1:1 to 1:10.

6. The method according to claim 1, wherein the active ingredients (a) and (b) are present in a synergistically effective amount.

* * * * *